United States Patent [19]

Cognion et al.

[11] 4,417,056

[45] Nov. 22, 1983

[54] PROCESS FOR PREPARING 2-(4-AMINOPHENYL)-5-AMINO-BENZIMIDAZOLE AND SUBSTITUTED DERIVATIVES

[75] Inventors: Jean-Marie Cognion, Saint-Genis-Laval; Pierre Durual, Vernaison, both of France

[73] Assignee: P.C.U.K. Produits Chimiques Ugine Kuhlmann, Courbevoie, France

[21] Appl. No.: 357,108

[22] Filed: Mar. 11, 1982

[30] Foreign Application Priority Data

Mar. 20, 1981 [FR] France ................................ 81 05587

[51] Int. Cl.$^3$ ............................................ C07D 235/18
[52] U.S. Cl. ......................................................... 548/334
[58] Field of Search .............................................. 548/334

[56] References Cited

U.S. PATENT DOCUMENTS 4,109,093  8/1978  Arsac et al. ............................ 548/334
4,192,947  3/1980  Bauer et al. ............................ 548/334

OTHER PUBLICATIONS

European Patent Application, No. 1, 246, (4-4-79).
Brown, *Chemical Abstracts*, vol. 59, (1963), p. 10065a.
Porai-Koshits et al., *Chemical Abstracts*, vol. 52, (1958), p. 17240.

*Primary Examiner*—Robert W. Ramsuer
*Attorney, Agent, or Firm*—Beveridge, DeGrandi and Kline

[57] ABSTRACT

The invention concerns a process for the preparation of 2-(4-aminophenyl)-5-aminobenzimidazole and substituted derivatives by catalytic cycloreduction of starting material N-(4-nitrobenzoyl)-2,4-dinitroaniline or a substituted derivative by hydrogen gas. According to the invention, the starting material is treated in suspension in an aqueous solution of hydrochloric or phosphoric acid, the content (C) of starting material in said suspension ranging from 0.15 to 1.5 mole per liter and the molar ratio (A): acid/starting material being from 2 to 20. The process is carried out at a hydrogen pressure from 5 to 100 bars and a temperature (T) from 20° to 150° C. selected so that the product $T \times A \times C$ is equal to or greater than 25. There is thereby obtained a product of excellent purity with very good yields.

11 Claims, No Drawings

PROCESS FOR PREPARING 2-(4-AMINOPHENYL)-5-AMINO-BENZIMIDAZOLE AND SUBSTITUTED DERIVATIVES

The present invention concerns a new process for preparing 2-(4-aminophenyl)-5-aminobenzimidazole (hereinafter referred to as DAPBI) and substituted derivatives thereof.

Several different methods of access to DAPBI or to its derivatives substituted by halogen atoms or by alkyl or alkoxy groups on the aromatic nuclei are known.

In French Pat. Nos. 2,297,849 and 2,332,273 (both corresponding to U.S. Pat. No. 4,109,093) a synthesis in two stages starting from N-(4-nitrobenzoyl)-2,4-dinitroaniline was proposed, consisting in (a) a chemical reduction by means of sodium or ammonium hydrosulfide, sulfide or polysulfide to $N_1$-(4-amino-benzoyl 1,2,4-triaminobenzene, and then (b) a cyclodehydration of this triamine in an acid medium leading to DAPBI or to one of its hydrochlorides. Unfortunately, this technique does not allow DAPBI molar yields, based on the trinitro compound used, greater than 80% to be obtained. In fact, the strongly basic reducing medium also causes secondary hydrolysis reactions which reduce both the yield and the quality of the product sought; the formation of p-aminobenzoic acid in a quantity which cannot be disregarded is ascertainable. Furthermore, this chemical reduction technique creates very large quantities of by-products in the form of effluents polluted by sulfur compounds whose purification before disposal is costly.

In the journal Zhur. Obshchei Khim 28, 928, 1958 (Chem. Abst. 52, 17240, 1958), B. A. Porai-Koshits and Ch. Frankovskii also proposed a chemical cycloreduction of N-(4-nitrobenzoyl)-2,4-dinitroaniline by the coupled $SnCl_2$, HCl. However, this technique presents serious drawbacks, namely: high cost of the opration since stannous chloride is not a current industrial product; high pollution by the by-products; and DAPBI molar yields limited to 74–75% based on the starting products p-nitro-benzoyl chloride and 2,4-dinitroaniline.

In U.S. Pat. No. 4,192,947 synthesis of DAPBI in a single stage starting from $N_1$-(4-nitrobenzoyl)-5-nitro-o-phenylenediamine was proposed by cycloreduction in a strongly basic medium, in an aqueous phase or in an organic solvent. 4-nitro-2,4-diamino-benzene, necessary for preparing $N_1$-(4-nitrobenzoyl)-5-nitro-o-phenylenediamine by condensation with p-nitrobenzoyl chloride, is an expensive raw material. On the other hand, the molar yields of DAPBI reported, based on nitro-diamino-benzene, are in the order of 84% with a purity of 91–92%.

The catalytic reduction of N-(4-nitrobenzoyl)-2,4-dinitroaniline by hydrogen gas is known (USSR Pat. No. 546,608 summarized in Chem. Abst. 87, 22808 t, 1977), but no industrial manufacture has been envisaged. It necessitates the use, in high quantity, of costly solvents such as N,N-dimethylformamide, N-methylpyrrolidone, aniline or dioxan and DAPBI cannot be obtained in a single stage; with often mediocre yields, the corresponding triamine is obtained, sometimes crystallized with solvent. It is also the triamine which is obtained when the reduction is carried out in very dilute acid medium under the conditions disclosed by Shchel'tsyn et al. in the Journal Sint. Anal. strukt. org. Soedin. 1972, No. 4, 64-8.

It has now been found that there can be obtained, in a single stage and without the presence of any organic solvent, a DAPBI of excellent purity with very good yields when N-(4-nitrobenzoyl)-2,4-dinitroaniline in suspension in an aqueous solution of hydrochloric or phosphoric acid is subjected to catalytic cycloreduction by hydrogen gas, in accordance with the following reaction diagram:

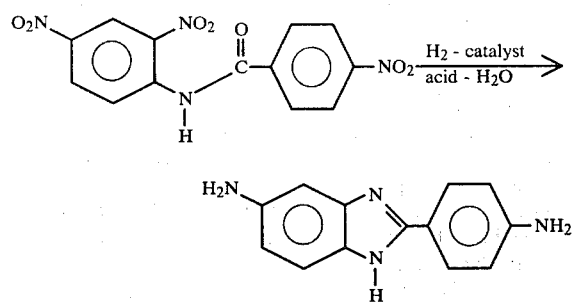

The catalysts which are useful in the process according to the invention are those which are conventionally used for the hydrogenation of nitro-aromatic functions to amines, that is to say, catalysts based on a metal belonging to group VIII of the Periodic Classification of the elements, such as, for example, nickel, platinum, palladium, rhodium and ruthenium. These metals may be used as such or deposited on supports such as, for example, alumina, silica alumina, magnesia, active carbon, etc. Bimetallic catalysts of the Pt-Pd type may also be used.

The quantity of metal used will be from 25 mg to 5 g per kg of N-(4-nitrobenzoyl)-2,4-dinitroaniline, but a quantity between 25 and 500 mg/kg is preferred.

The content (C) of N-(4-nitrobenzoyl)-2,4-dinitroaniline in the acid aqueous suspension will vary from 0.15 to 1.5 mole per liter. The molar ratio (A): acid/N-(4-nitrobenzoyl)-2,4-dinitroaniline will be from 2 to 20.

The process is carried out at a hydrogen pressure ranging from 5 to 100 bars, preferably from 20 to 50 bars, and at a temperature (T) from 20° to 150° C. which is selected so that the product $T \times A \times C$ is equal to or greater than 25. Preferably, the temperature is selected between 20° and 100° C. so that the product $T \times A \times C$ is equal to or greater than 50.

The hydrogenation rates are high and the DAPBI salt formed during the reaction immediately goes into solution. When the reaction is completed, simple hot filtration permits separation and recovery of the catalyst. By cooling and possibly evaporating the filtrate, the DAPBI salt in crystallized form can be recovered. The DAPBI can be isolated in the form of a free base by any well-known method. For manufacturing azo dyes one can also use the filtrate as it is.

The present invention also includes the preparation of DAPBI substituted derivatives starting from the corresponding substituted derivatives of N-(4-nitrobenzoyl)-2,4-dinitroaniline. Said derivatives include substitution by halogen (chlorine, bromine, iodine and fluorine), by alkyl containing 1 to 4 carbon atoms and alkoxy containing 1 to 4 carbon atoms.

The following examples, in which the percentages indicated are by weight, illustrate the invention, without limiting it.

EXAMPLE 1

Into a 1 liter Hastelloy C autoclave, fitted with a magnetic rotary stirring device and an oil-circulation heating device were placed 20 g (0.06 mole) of N-(4-nitrobenzoyl)-2,4-dinitroaniline, 135 g of water, 45 g of a 35.5% HCl solution (0.44 mole) and 0.2 g of a Pd/active carbon catalyst containing 50% water and 2.5% palladium. After scavenging with nitrogen, hydrogen was introduced at a pressure of 30 bars and the mixture was heated to 90° C. As soon as this temperature was reached, activation of the stirrer caused a fall in hydrogen pressure which was kept at 30 bars by making up the shortfall. After 4 hours of reaction, hydrogen consumption ceased and in the autoclave was recovered a hot solution which was immediately separated from the catalyst in suspension by filtration. After cooling and evaporating, 20.6 g (0.06 mole) of DAPBI trihydrochloride, identified by infrared spectrography, was obtained from this solution.

5 g (0.015 mole) of this trihydrochloride were again put into aqueous solution and neutralized to pH 11 by 50 ml of a normal sodium hydroxide solution (0.05 mole). After filtration, washing with water and recrystallizing from ethanol, 3.45 g (0.0143 mole) of DAPBI crystallized with a mole of water were recovered. The infrared spectrum agreed well with that of the product obtained by chemical reduction according to French Pat. No. 2,297,849. Elementary analysis gave values corresponding well to the empirical formula $C_{13}H_{12}N_4$, $H_2O$ of molecular weight 242:

|     | Calculated | Found |
| --- | --- | --- |
| % C | 64.46 | 64.44 |
| % H | 5.78 | 5.89 |
| % N | 23.14 | 22.84 |

The nature and purity of the product obtained were also confirmed by NMR.

EXAMPLE 2

Into the autoclave described in Example 1, 60 g (0.18 mole) of N-(4-nitrobenzoyl)-2,4-dinitroaniline, 405 g of water, 135 g of a 35.5% HCl solution (1.3 mole) and 0.6 g of the same catalyst as in Example 1 were introduced. After 5.5 hours of reaction in the same conditions as in Example 1 (90° C. and 30 bars), filtration of the catalyst, cooling and evaporation, 60.5 g (0.18 mole) of DAPBI trihydrochloride identified by infrared spectrography, were obtained.

EXAMPLE 3

Into the autoclave described in Example 1, 60 g (0.18 mole) of N-(4-nitrobenzoyl)-2,4-dinitroaniline, 135 g of water, 70 g of a 35.5% HCl solution (0.68 mole) and 0.6 g of the same catalyst as in Example 1 were introduced. After 4 hours of reaction in the same conditions as in Example 1 (90° C. and 30 bars), filtration of the catalyst, cooling and evaporation, 60 g (0.18 mole) of DAPBI trihydrochloride, identified by infrared spectrography, were obtained.

EXAMPLE 4

The procedure was as in Example 1, except that the 0.2 g of palladium catalyst was replaced by 0.1 g of a dry catalyst containing 5% rhodium on active carbon (95%). After 3.5 hours of reaction, 20 g of DAPBI trihydrochloride, identified by infrared spectrography, were obtained.

EXAMPLE 5

The procedure was the same as in Example 1 except that the 0.2 g of palladium catalyst was replaced by 0.1 g of a dry catalyst containing 5% platinum on active carbon (95%). After 2.25 hours of reaction, 20 g of DAPBI trihydrochloride, identified by infrared spectrography, were obtained. 10 g (0.03 mole) of this trihydrochloride were put into aqueous solution and neutralized to pH 10 by 90 ml of a normal sodium hydroxide solution. After filtration and washing with water, 7 g (0.029 mole) of DAPBI crystallized with a mole of water were recovered. The infrared and NMR spectra of this product agreed well with the DAPBI spectra obtained previously.

EXAMPLE 6

Example 1 was repeated at three different temperatures (90°, 50° and 20° C.). The 0.2 g of palladium catalyst was replaced by 0.25 g of a bimetallic catalyst containing 2% palladium and 0.2% platinum on active carbon (97.8%), this catalyst being introduced into the reactor in the form of an aqueous solution containing 35 g of solid per liter. The results obtained are shown in the following Table 1.

TABLE 1

| T °C. | Duration in hours | DAPBI trihyrochloride g | mole |
| --- | --- | --- | --- |
| 90 | 0.75 | 20 | 0.06 |
| 50 | 2 | 18.10 | 0.055 |
| 20 | 2.5 | 20 | 0.06 |

EXAMPLE 7

Into the autoclave described in Example 1, 20 g (0.06 mole) of N-(4-nitrobenzoyl)-2,4-dinitroaniline, 135 g of water, 87 g of commercial 85% phosphoric acid (0.76 mole) and 0.4 g of the same catalyst as in Example 1 were introduced.

After 1.75 hours of reaction under the same conditions as in Example 1 (90° C. and 30 bars), filtration of the catalyst, washing with water and cooling, 238 ml of a solution of DAPBI phosphate were obtained which was titrated by liquid phase chromatography under pressure according to the reverse-phase method with matching of ions by using sodium heptanesulfonate as gegenion. The solution contained 46.4 g of DAPBI per liter; that corresponded to 0.0493 mole of DAPBI, that is a yield of 82.2%.

EXAMPLE 8

Into the autoclave described in Example 1, 10 g (0.03 mole) of N-(4-nitrobenzoyl)-2,4-dinitroaniline, 130 g of water, 14 g of commercial 85% phosphoric acid (0.12 mole) and 0.8 g of the same catalyst as in Example 1 were introduced.

After 15 minutes of reaction under the same conditions as in Example 1 (90° C., 30 bars), filtration, washing with water and cooling, 345 ml of a solution of DAPBI phosphate were obtained. The content of this solution, determined by liquid phase chromatography, was 15.8 g of DAPBI per liter; that corresponds to 0.0243 mole of DAPBI, that is a yield of 81%.

EXAMPLE 9

10 g (0.03 mole) of N-(4-nitrobenzoyl)-2,4-dinitroaniline, 150 g of water, 43.5 g of commercial phosphoric acid (0.38 mole) and 0.4 g of the same catalyst as in Example 1 were introduced into the autoclave described in Example 1.

After one hour of reaction under the same conditions as in Example 1 (90° C., 30 bars), filtration of the catalyst and cooling, 186 ml of a solution of DAPBI phosphate were obtained. Its content in DAPBI, determined by liquid phase chromatography, was 33.5 g/l; that corresponds to 0.278 mole of DAPBI, that is a yield of 92.7%.

What is claimed is:

1. In a process for the preparation of 2-(4-aminophenyl)-5-amino-benzimidazole and substituted derivatives thereof by cycloreduction of starting material N-(4-nitrobenzoyl)2,4-dinitroaniline or a substituted derivative thereof by means of hydrogen gas in the presence of a catalyst based on a metal belonging to Group VIII of the Periodic Classification of the elements, the improvement which comprises suspending said starting material in an aqueous solution of hydrochloric acid or phosphoric acid, the content (C) of starting material in said suspension ranging from 0.15 to 1.5 mole per liter and the molar ratio (A): acid/starting material ranging from 2 to 20, said reduction being conducted at a hydrogen pressure from 5 to 100 bars and at a temperature (T) from 20° to 150° C. selected whereby the product $T \times A \times C$ is equal to or greater than 25.

2. The process according to claim 1 in which the catalyst used in based on a metal selected from nickel, platinum, palladium, rhodium and ruthenium.

3. The process according to claim 2 in which the catalyst consists of platinum, palladium or rhodium deposited on a support.

4. The process according to claim 2 in which the catalyst consists of platinum and palladium deposited on a support.

5. The process according to claim 1, 2, 3 or 4 in which 25 to 500 mg of metal per kg of starting material are used.

6. The process according to claim 5 in which the process is carried out at a hydrogen pressure from 20 to 50 bars.

7. The process according to claim 6 in which the process is carried out at a temperature (T) from 20° to 100° C. selected so that the product $T \times A \times C$ is equal to or greater than 50.

8. The process according to claim 5 in which the process is carried out at a temperature (T) from 20° to 100° C. selected so that the product $T \times A \times C$ is equal to or greater than 50.

9. The process according to claim 7 wherein a solution of a hydrochloride or phosphate of 2-(4-aminophenyl)-5-aminobenzimidazole or substituted derivative thereof is obtained.

10. The process according to claim 9 in which the 2-(4-aminophenyl)-5-aminobenzimidazole or its substituted derivative is isolated in the form of a salt.

11. The process according to claim 10 wherein 2-(4-aminophenyl)-5-aminobenzimidazole or substituted derivative is isolated in the form of its trihydrochloride.

* * * * *